(12) United States Patent
Predick

(10) Patent No.: US 11,998,221 B2
(45) Date of Patent: Jun. 4, 2024

(54) ARTICULATING CURETTE FOR DECORTICATING A VERTEBRAL ENDPLATE VIA A CANNULA

(71) Applicant: Life Spine, Inc., Huntley, IL (US)

(72) Inventor: Daniel P. Predick, Wheat Ridge, CO (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 17/945,557

(22) Filed: Sep. 15, 2022

(65) Prior Publication Data

US 2023/0157710 A1     May 25, 2023

Related U.S. Application Data

(60) Provisional application No. 63/282,343, filed on Nov. 23, 2021.

(51) Int. Cl.
*A61B 17/88* (2006.01)
*A61B 17/16* (2006.01)
(Continued)

(52) U.S. Cl.
CPC ...... *A61B 17/1671* (2013.01); *A61B 17/1757* (2013.01); *A61F 2002/4627* (2013.01)

(58) Field of Classification Search
CPC .... A61B 17/885; A61B 17/8852–8858; A61B 17/1671; A61B 17/1659
See application file for complete search history.

(56) References Cited

U.S. PATENT DOCUMENTS 6,575,978 B2 * 6/2003 Peterson ............ A61B 17/1604
606/171
11,234,716 B2 * 2/2022 Kahmer ............ A61B 17/1671
(Continued)

FOREIGN PATENT DOCUMENTS

WO     2020061464 A1     3/2020

OTHER PUBLICATIONS

International Search Report and Written Opinion of the International Searching Authority, European Patent Office, dated Nov. 15, 2022.

*Primary Examiner* — Eduardo C Robert
*Assistant Examiner* — Michelle C Eckman
(74) *Attorney, Agent, or Firm* — Foley & Lardner LLP

(57) ABSTRACT

A medical instrument fashioned as an articulating curette for decorticating vertebral endplates of vertebrae of a spine via a cannula has a handle, a controller connected to the handle, two opposing arms extending from the controller, a control shaft between the two opposing arms and coupled to the controller for longitudinally axial movement thereof by the controller relative to the two opposing arms, a bladed decorticating head for decorticating vertebral endplate bone material from vertebral endplates and pivotally connected to the two opposing arms for articulation from 0° to 90° relative to the longitudinal axis of the control shaft, and a pivot mechanism between the bladed decorticating head and the control shaft providing controlled articulation of the bladed decorticating head through longitudinally axial movement of the control shaft. Rotational movement of the controller moves the control shaft axially relative to the two opposing arms to articulate the bladed decorticating head.

14 Claims, 7 Drawing Sheets

(51) Int. Cl.
*A61B 17/17* (2006.01)
*A61F 2/46* (2006.01)

(56) References Cited

U.S. PATENT DOCUMENTS

| | | | | |
|---|---|---|---|---|
| 2002/0032447 | A1* | 3/2002 | Weikel | A61B 17/7061 606/86 R |
| 2005/0113838 | A1* | 5/2005 | Phillips | A61B 17/22031 606/86 R |
| 2008/0077241 | A1* | 3/2008 | Nguyen | A61F 2/4684 606/85 |
| 2008/0294167 | A1* | 11/2008 | Schumacher | A61B 17/1617 606/167 |
| 2015/0173808 | A1* | 6/2015 | Sack | A61B 17/88 606/86 A |
| 2021/0169459 | A1* | 6/2021 | Pacheco-Serrant | A61B 17/1617 |

* cited by examiner ately axial movement of the control shaft by the controller relative to the two opposing arms, a decorticating head having a blade for decorticating and/or preparing vertebral endplates of vertebrae and pivotally connected to the two arm ends of the two opposing arms for articulation thereof relative to the two opposing arms, and a pivot mechanism situated on and between the decorticating head and the control shaft distal end for providing controlled articulation of the decorticating head through longitudinally axial movement of the control shaft.

ARTICULATING CURETTE FOR DECORTICATING A VERTEBRAL ENDPLATE VIA A CANNULA

CROSS-REFERENCE TO RELATED APPLICATIONS

This U.S. non-provisional patent application claims the benefit of and/or priority under 35 U.S.C. § 119(e) to U.S. provisional patent application Ser. No. 63/282,343 filed Nov. 23, 2021 titled "Articulating Curette," the entire contents of which is specifically incorporated herein by reference.

FIELD OF THE INVENTION

The present invention relates to medical instruments for spine procedures and, more particularly, to medical instruments for decorticating vertebral endplates of vertebrae of a spine via a cannula.

BACKGROUND OF THE INVENTION

Many people contend with spine issues due to age, disease, trauma, congenital, and acquired complications and conditions. While some spine issues can be alleviated without surgery, other spine issues necessitate surgery. Spine surgery may entail removing vertebral disc material from between adjacent vertebrae. This is now typically accomplished using minimally invasive surgery, micro invasive surgery or similar surgery. All such methods reduce trauma by using surgical instruments that are introduced into the body via one or more small incisions. Certain of these medical instruments are introduced into the body via a separate cannula, endoscope or the like (collectively, cannula) that has been inserted into the body through a small incision and positioned accordingly. The medical instrument is then inserted into the cannula and operated accordingly.

In cases where a vertebral disc is to be replaced with an interbody spine implant, the vertebral area needs to be prepared before the interbody spine implant is inserted in the vertebral disc space between the adjacent vertebrae. First, the vertebral disc and/or vertebral disc material is removed from the vertebral disc space of adjacent vertebrae, then the endplates of the adjacent vertebra facing the vacated vertebral disc space are decorticated or prepared for receiving the interbody spine implant. With both procedures, an appropriate medical instrument is used via the cannula. When preparing the vertebral end plates, a medical instrument with a head designed to decorticate the vertebral endplate is extended from the open end of the cannula where the head is manipulated to decorticate/prepare the vertebral endplates.

Heretofore, medical instruments for decorticating/preparing vertebral endplates have been limited in efficacy and/or efficiency. In one respect, such prior medical instruments are limited in the amount of vertebral endplate material they can remove in a single swipe. In another respect, such prior medical instruments are limited in their reach relative to the associated cannula. In still another respect, such prior medical instruments are limited in ease of use. Other limitations exist.

It would therefore be advantageous to have a better medical instrument for decorticating and/or preparing vertebral endplates through a vertebral disc space via a cannula in a minimally, micro or other surgical spine procedure that reduces surgical complexity. It would furthermore be advantageous to have a medical instrument for a minimally or micro invasive or similar spine procedure that provides greater removal of vertebral endplate material, greater degree of sweep, and extension beyond the perimeter of the cannula used with the medical instrument.

The present medical instrument addresses the above and more.

SUMMARY OF THE INVENTION

A medical instrument in the form of an articulating curette for decorticating and/or preparing a vertebral endplate of a vertebra of a spine, particularly, but not necessarily, during minimally invasive spine surgery, micro invasive spine surgery or similar spine procedure, has a handle, a controller connected to the handle, two opposing arms extending from the controller and defining two arm ends distal to the controller, a control shaft defining a distal control shaft end and a proximal control shaft end and disposed between the two opposing arms, the control shaft proximal end operably coupled to the controller for longitudinally axial movement of the control shaft by the controller relative to the two opposing arms, a decorticating head having a blade for decorticating and/or preparing vertebral endplates of vertebrae and pivotally connected to the two arm ends of the two opposing arms for articulation thereof relative to the two opposing arms, and a pivot mechanism situated on and between the decorticating head and the control shaft distal end for providing controlled articulation of the decorticating head through longitudinally axial movement of the control shaft.

Rotational movement of the controller moves the control shaft axially relative to the two opposing arms to articulate the decorticating head relative to the two opposing arms and the control shaft, wherein the decorticating head pivots from and between 0° and 90° positions relative to the longitudinal axis of the control shaft whereby the decorticating head sweeps along an arc beyond a diameter or perimeter of the cannula after the decorticating head has been extended from the cannula. Rotational movement of the controller in a first direction moves the control shaft in a first longitudinally axial direction to sweep the decorticating head from the 0° position to the 90° position, while rotational movement of the controller in a second direction moves the control shaft in a second longitudinally axial direction to sweep the decorticating head from the 90° position to the 0° position. Prepping the vertebral endplate by the decorticating head occurs during movement or swipes of the decorticating head at any position from 0° to 90°.

In one form, the pivot mechanism includes two opposing slots in a bifurcated proximal end of the decorticating head, the bifurcated proximal end pivotally connected to the two arm ends of the two opposing arms, and a pivot pin on the distal control shaft end that extends into the two opposing slots. The opposing slots are situated at an angle relative to the longitudinal axis of the two opposing arms and control shaft. Longitudinal axially movement of the control shaft moves the pivot pin within the opposing slots to provide the arcuate motion of the decorticating head.

In one form, the decorticating head has an opening for collecting shaved vertebral endplate material from the vertebra.

The articulating curette is sized for use, preferably, but not necessarily, with a cannula.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention and its features will be better understood by reference to the accompanying drawings, wherein.

Figure 1:
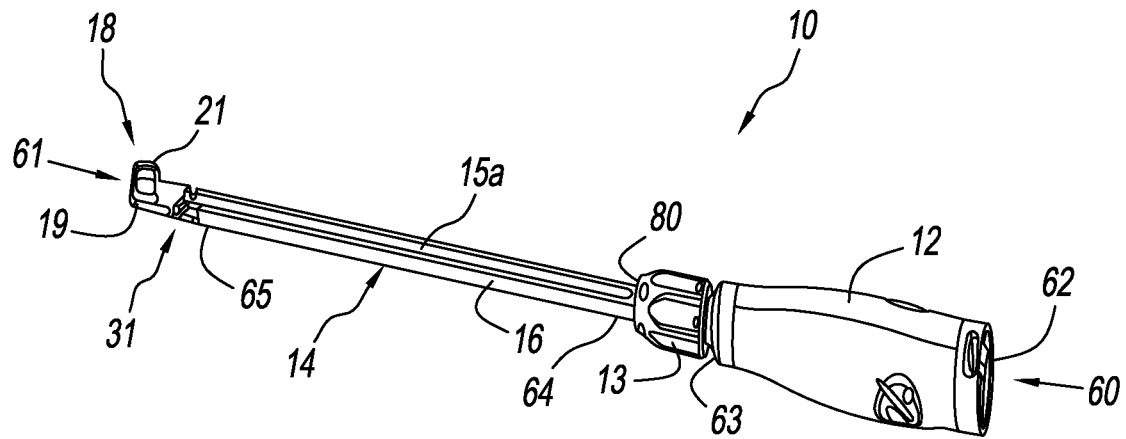
FIG. 1 is a view of a medical instrument, fashioned in accordance with the present principles, formed as an articulating curette for decorticating vertebral endplates from a vertebra of a spine during spine surgery using a cannula.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described embodiment, and any further applications of the principles of the invention as described herein are contemplated as would normally occur to one skilled in the art to which the invention relates.

DETAILED DESCRIPTION OF THE INVENTION

Referring to FIG. 1, there is shown a medical instrument in the form of an articulating curette, generally designated 10, for decorticating and/or preparing (collectively, decorticating) vertebral endplates (not shown) of vertebrae (not shown) of a spine (not shown) during a surgical spine procedure, particularly, but not necessarily, in minimally invasive spine surgery, micro spine surgery, or the like (surgical spine procedure) with the use of a cannula, endoscope, or the like (collectively, cannula). The articulating curette 10 is made from one or more surgical grade materials, and overall defines a proximal end 60 and a distal end 61.

The articulating curette 10 has a handle 12 defining a proximal end 62 and a distal end 63, a controller 13 coupled to the distal end 63 of the handle 12, a shaft assembly 14 defining a proximal end 64 connected to a distal end 80 of the controller 13 opposite the handle 12, a decorticating head or end 18 at a distal end 65 of the shaft assembly 14 with the decorticating head 18 having a decorticating, shaving, or blade structure 21, and a pivot mechanism 31 pivotally coupling the decorticating head 18 with the distal end 65 of the shaft assembly 14 for articulating the decorticating head 18 about and relative to the distal end 65 of the shaft assembly 14. The decorticating head 18 defines a proximal end 66 and a distal end 67. The shaft assembly 14 has first and second opposing arms 15a, 15b and a control shaft 16 situated between the first and second opposing arms 15a, 15b, the nomenclature first and second being arbitrary here and throughout unless specifically indicated otherwise.

As best depicted in FIGS. 3-6, 7-9, and 11-14, once the decorticating head 18 extends beyond the cannula 50, the decorticating head 18 and therefore the decorticating structure 21, is able to sweep an arc of 0° to 90° from a longitudinal axis LA of the shaft assembly 14 and beyond the diameter or perimeter of the cannula 50. Decorticating a vertebral endplate by the decorticating head 18 can occur at any position from 0° to 90°, but is typically accomplished during a sweep of the decorticating head 18 from the 0° position to the 90° position.

Figure 2:
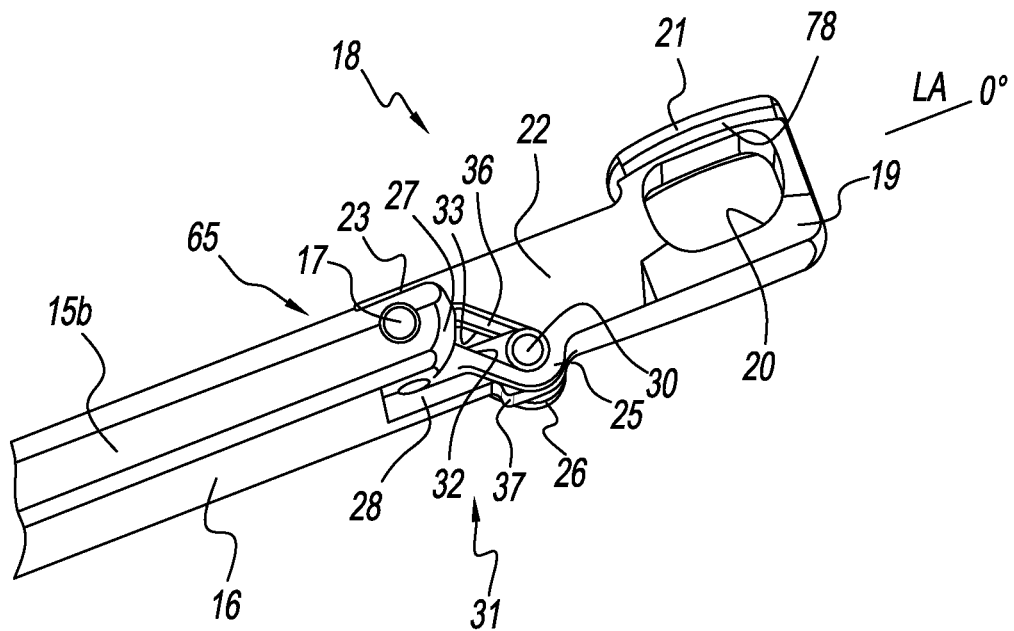
FIG. 2 is an enlarged view of a distal end of the articulating curette of FIG. 1 with a decorticating head thereof in an axially 0° position.

Turning to FIG. 2, the distal end 65 of the shaft assembly 14 with the decorticating head 18 and pivot mechanism 31 is specifically shown. The decorticating head 18 has a body 19 with the decorticating structure 21 situated generally transverse to the longitudinal axis LA of the shaft assembly 14 and essentially on a distal end 67 of the body 19. The decorticating structure 21 may be slightly curved and includes a first blade 78 on a first underside of the decorticating structure 21, and a second blade 79 on a second underside of the decorticating structure 21. The first and second blades 78, 79 are configured to scrape against the vertebral endplate during a swipe from 0° to 90°. An opening 20 is adjacent the first and second blades 78, 79 that can collect shaven vertebral endplate material and/or allow shaven (decorticated) vertebral endplate material to pass therethrough for collection by another medical instrument (not shown). The body 19 has a bifurcated proximal end 66 that is pivotally connected to the arms 15a, 15b. Particularly, the decorticating head 18 includes a neck 22 that splits into a first leg 23 and a second leg 24 which are opposite each other and defines an opening 36 between the first and second leg 23, 24. The first leg 23 is pivotally attached to a distal, curved end 27 of the second arm 15b, while the second leg 24 is pivotally attached to a distal, curved end 29 of the first arm 15a, each by a pivot pin 27 extending through the first leg 23, the end 27, the second leg 24, and the end 29. A first boss 25 is situated in the distal end of the first leg 23 adjacent the neck 22, while a second boss 26 is situated in the distal end of the second leg 24 adjacent the neck 22. A first slot 32 is provided in the first leg 23 that extends at an angle from the first boss 25 relative to the longitudinal axis LA of the shaft assembly 14 towards the proximal end 64 of the shaft assembly 14. A second slot 33 is provided in the second leg 24 that extends at an angle from the second boss 26 relative to the longitudinal axis LA of the shaft assembly 14 toward the proximal end 64 of the shaft assembly 14. The angle of the first and second slots 32, 33 are the same.

The control shaft 16 has a stem 28 on its distal end that is received in the opening 36 between the first and second legs 23, 24. The distal end of the stem 28 has a flange 37 with a pin 30. The flange 37 is situated in the opening 36, while the pin 30 extends into the first and second slots 32, 33. Longitudinally axial movement of the control shaft 16 controls articulation of the decorticating head 18 about the first and second arms 15a, 15b. In FIG. 2, the control shaft 16 is in its axially most forward or furthermost position wherein the shaving head is in the 0° position (co-axial with the longitudinal axis LA of the shaft assembly 14). The pin 30 is at its travel end within the first and second slots 32, 33 at the first and second bosses 25, 26.

Figure 3:
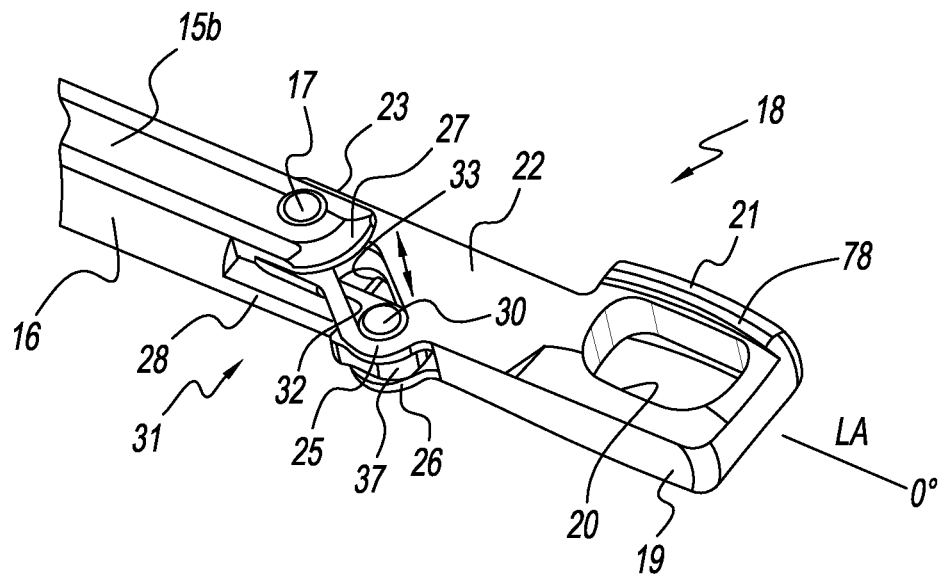
FIG. 3 is an enlarged view of the decorticating head of the articulating curette of FIG. 1 with the decorticating head in an axially straight or 0° position.
Figure 4:
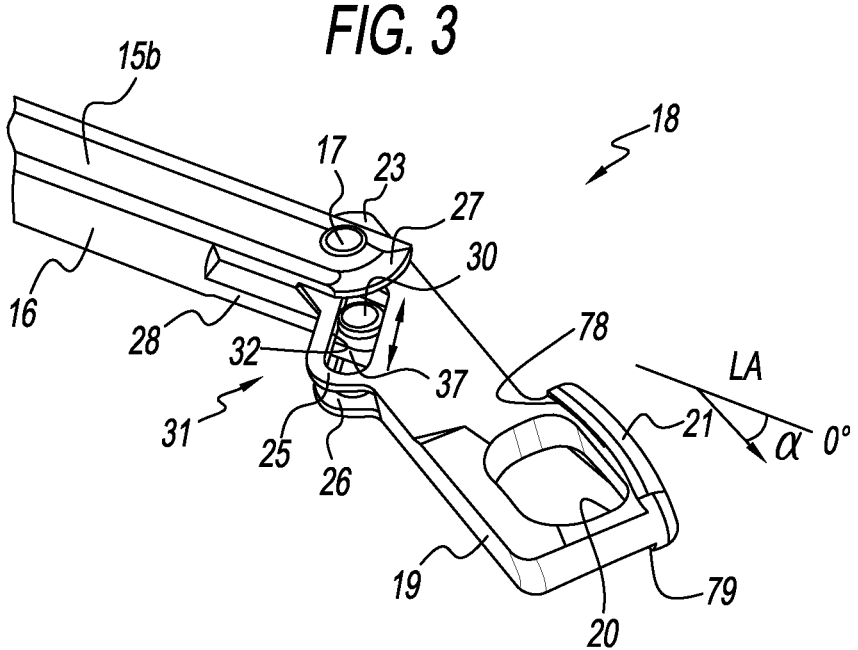
FIG. 4 is another enlarged view of the decorticating head of the articulating curette of FIG. 1 with the decorticating head in an axially angled position between 0° and 90°.
Figure 5:
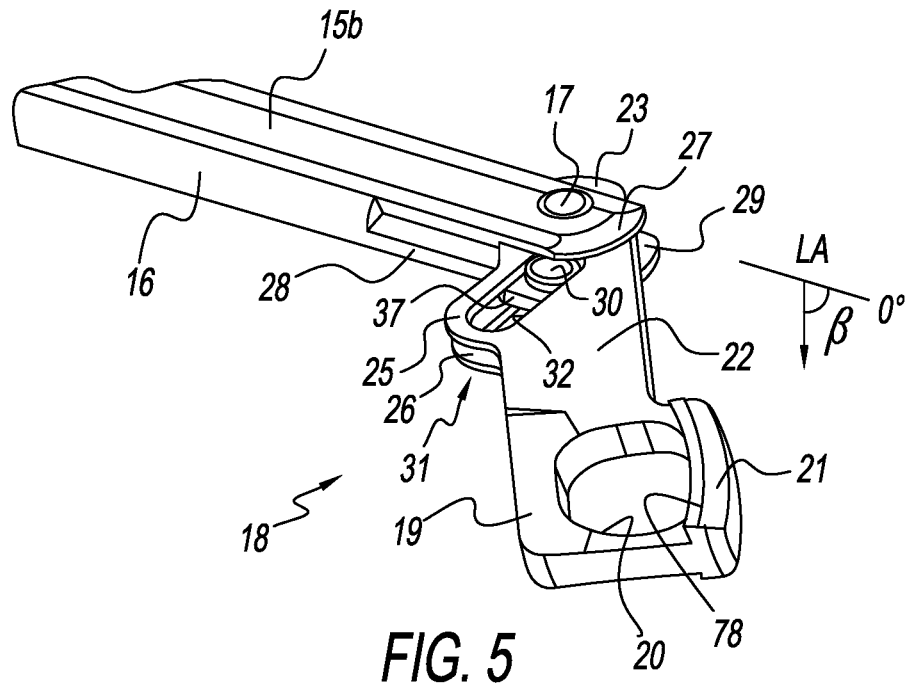
FIG. 5 is another enlarged view of the decorticating head of the articulating curette of FIG. 1 with the decorticating head in another axially angled position between 0° and 90°.
Figure 6:
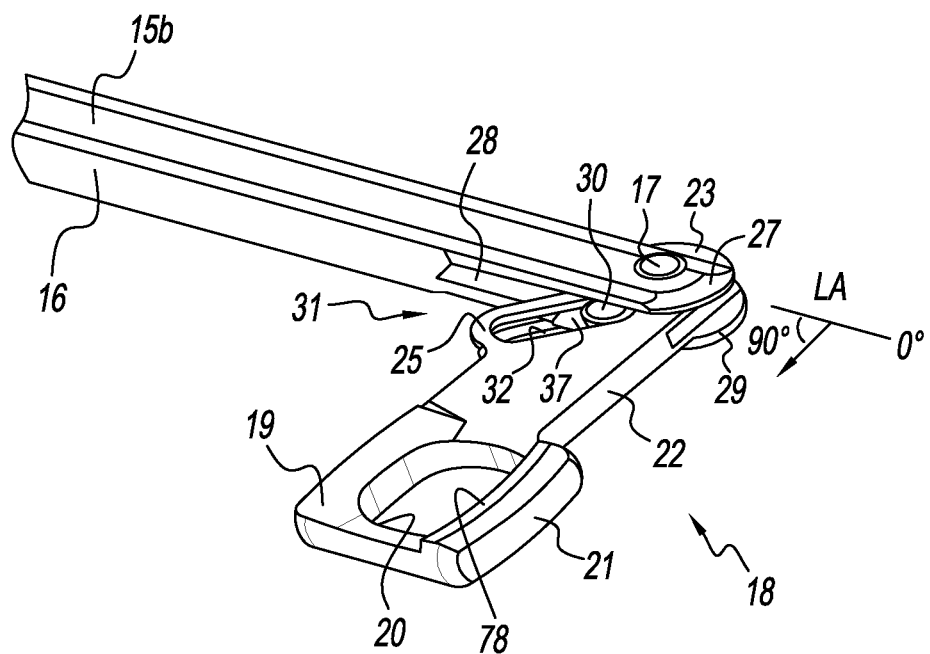
FIG. 6 is another enlarged view the decorticating head of the articulating curette of FIG. 1 with the decorticating head in an axially angled 90° position.

FIGS. 3-6 depict a sequence of articulation of the decorticating head 18 from its 0° position to its 90° position. In FIG. 3, the control shaft 16, through manipulation the controller 13, is in its furthermost axial position wherein the decorticating head 18 is in the 0° position. In FIG. 4, the control shaft 16, through manipulation of the controller 13, has been axially moved rearward (towards the handle 12 or the proximal end of the medical instrument 10). Since the decorticating head 18 is fixed in position relative to the first and second arms 15a, 15b, axially rearward movement of the control shaft 16, axially moves the stem 28 and thus the pin 30 rearward. The pin 30 thus pulls against the decorticating head 18 via the first and second slots 32, 33 such that the decorticating head 18 is caused to articulate (pivot) downward. FIG. 4 depicts the decorticating head 18 at an angle α relative to the 0° position. Further longitudinally axial movement of the control shaft 16 towards the handle 12 further causes the pin 30 to pull against the first and second slots 32, 33 to further articulate the decorticating head 18 downward. This is depicted in FIG. 5 where the decorticating head 18 has now been articulated into an angle β relative to the 0° position, with angle β greater than angle α. Still further, longitudinally axial movement of the control shaft 16 towards the handle 12 further causes the pin 30 to pull against the first and second slots 32, 33 to further articulate the decorticating head 18 downward. This is depicted in FIG. 6 where the decorticating head 18 has now been articulated into a final angular position of 90°. At this point, vertebral endplate bone material has been removed (decorticated) from the vertebral endplate, with the removed vertebral endplate bone material accumulating in the opening 20 of the decorticating head 18. Moving the control shaft 16 in the opposite longitudinally axial direction swings the decorticating head 18 from the 90° position to the 0° position.

Figure 7:
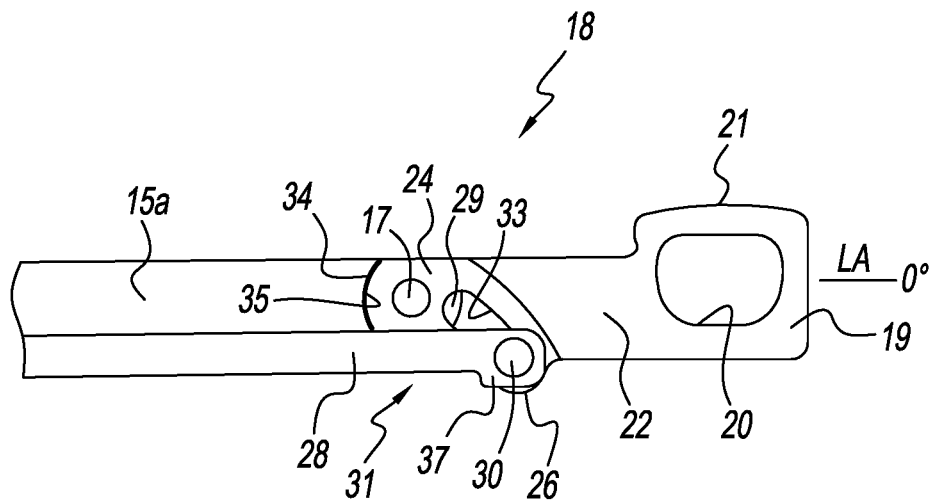
FIG. 7 is an enlarged side view of the decorticating head of the articulating curette of FIG. 1 with the decorticating head in the axially straight or 0° position.
Figure 8:
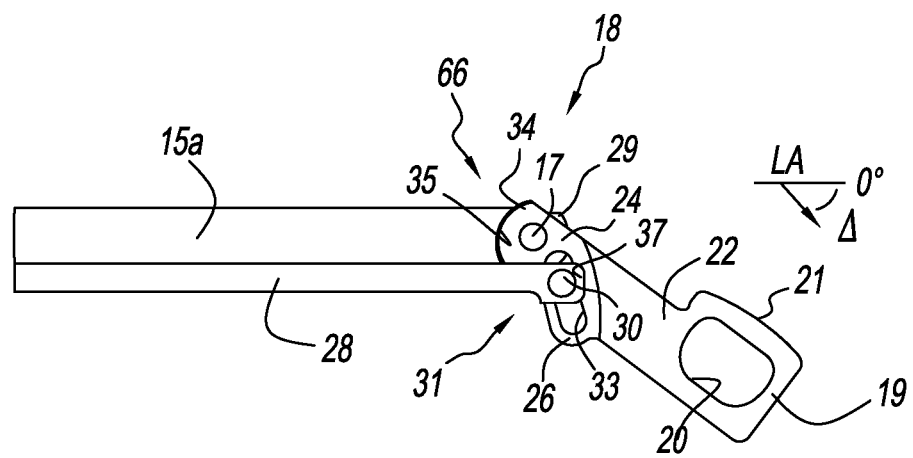
FIG. 8 is another enlarged side view of the decorticating head of the articulating curette of FIG. 1 with the decorticating head in an axially angled position between 0° and 90°.
Figures 9, 10:
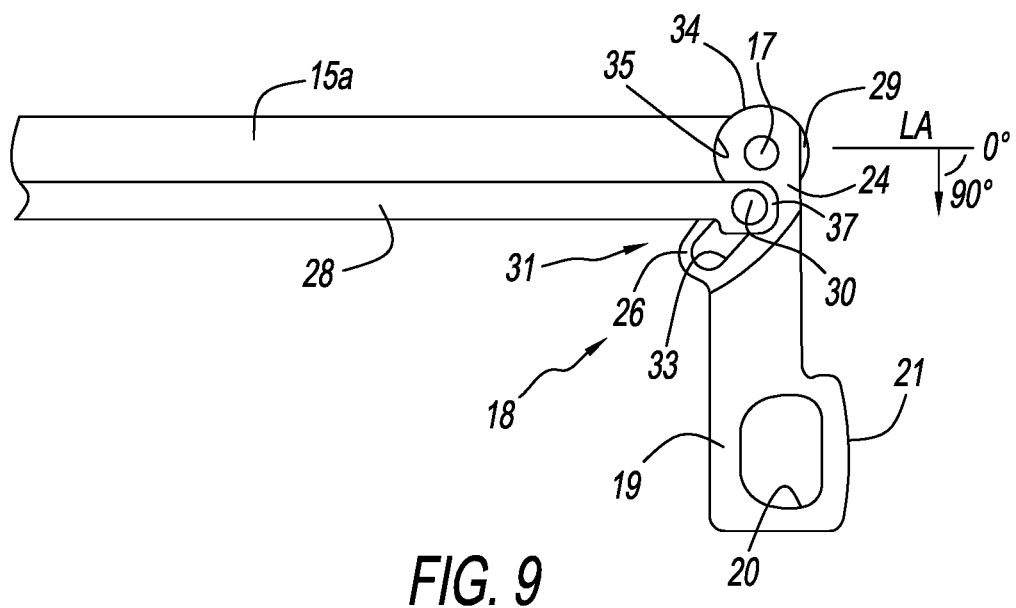
FIG. 9 is another enlarged side view of the decorticating head of the articulating curette of FIG. 1 with the decorticating head in the axially angled 90° position.
FIG. 10 is an enlarged end view of only the decorticating head of the articulating curette of FIG. 1 in the axially 0° position.

FIGS. 7-9 show the articulation (pivoting) of the decorticating head 18 from the 0° position to the 90° position with an intermediate angular position of angle Δ. The decorticating head 18, pivot mechanism 31, and distal end of the control shaft 16 are shown with the first arm 15b removed.

FIG. 10 depicts a perspective view of the distal end 65 of the shaft assembly 14 with the end in sectional. The control shaft 16 is slidingly connected to a main shaft 15 by a dovetail configuration that extends from the controller 13. The main shaft 15 has a dovetail groove 40 extending along the longitudinal length of the main shaft 15. The control shaft 16 has a dovetail flange 38 that is received in the dovetail groove 40. This provides a positive engagement of the control shaft 16 to the main shaft 15.

Figure 11:
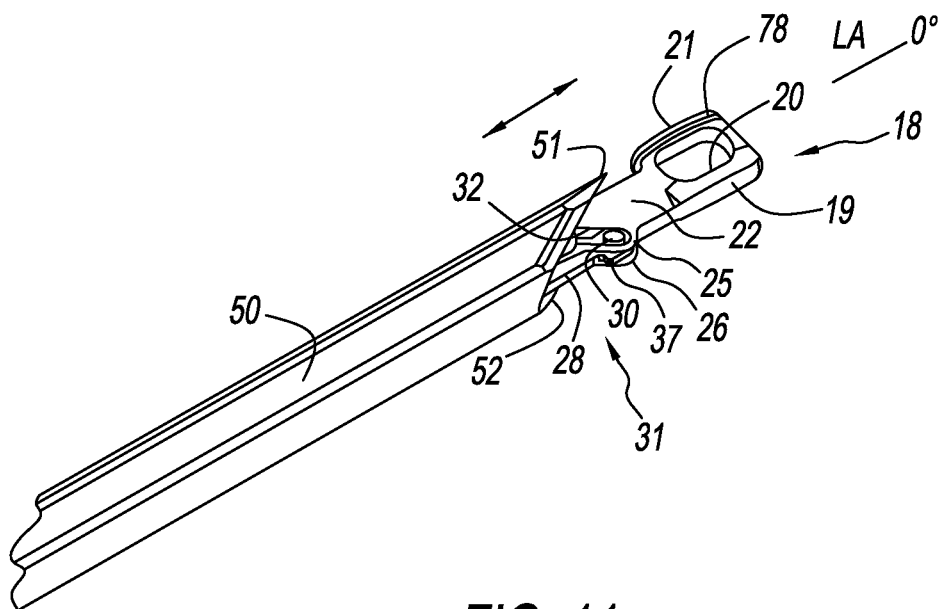
FIG. 11 is a view of the decorticating head of the articulating curette of FIG. 1 emerging from a cannula with the decorticating head in the axially 0° position.
Figure 12:
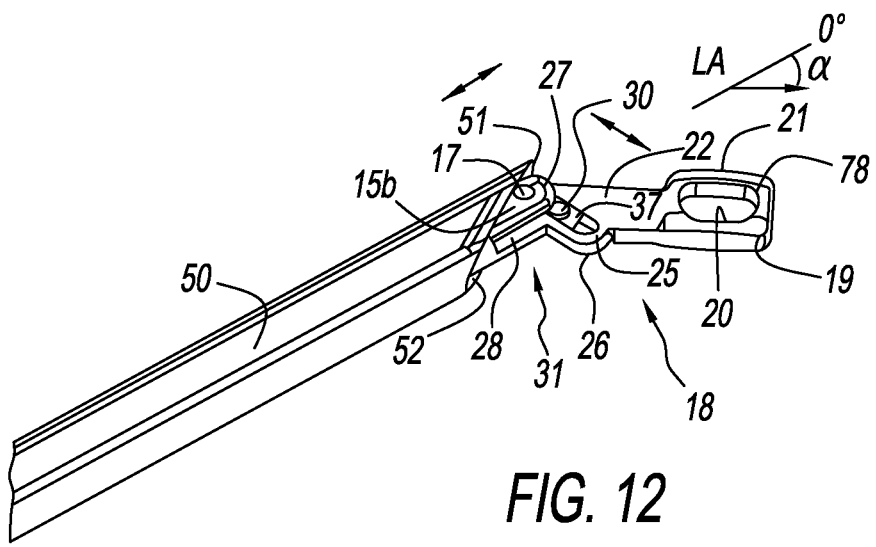
FIG. 12 is another view of the decorticating head of the articulating curette of FIG. 1 emerging from the cannula with the decorticating head in an axially angled position between 0° and 90°.
Figure 13:
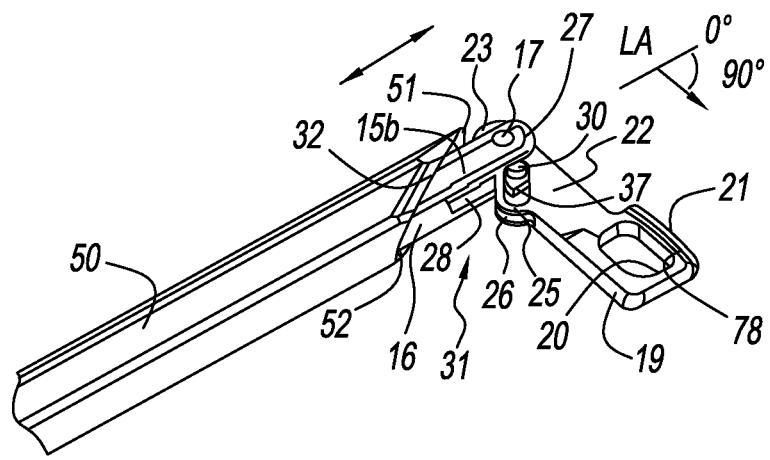
FIG. 13 is another view of the decorticating head of the articulating curette of FIG. 1 emerging from the cannula with the decorticating head in the axially angled 90° position.
Figure 14:
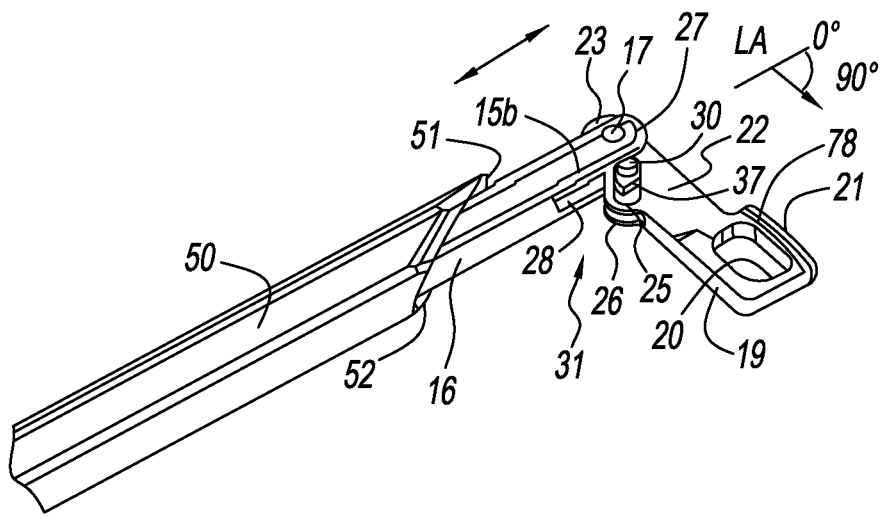
FIG. 14 is another view of the decorticating head of the articulating curette of FIG. 1 fully extended from the cannula with the decorticating head in the axially angled 90° position.

FIGS. 11-14 show the decorticating head 18 emerging from the cannula 50, such as during a minimally or micro invasive spine procedure. The cannula 50 has a longitudinal bore 52 and a slanted distal end 51. Movement of the decorticating head 18 through the cannula 50 is designated by the double-headed arrow adjacent the cannula/shaving head. FIG. 11 shows the decorticating head 18 beginning to emerge from the end 51 of the cannula 50. The decorticating head 18 is at the 0° position. FIG. 12 shows the decorticating head 18 emerged from the end 51 of the cannula 50 and positioned at the angle α. FIG. 13 shows the decorticating head 18 positioned at the 90° angle. FIG. 14 shows the decorticating head 18 at the 90° position and fully extended from the end 51 of the cannula 50. Retraction of the decorticating head 18 into the cannula 50 is by the reverse process.

One method of removing vertebral endplate material from a vertebral endplate of a vertebra of a spine (decorticating a vertebral endplate) includes positioning the cannula 50 adjacent a vertebral disc space (not shown) or vertebral endplate (not shown) of a spine (not shown); inserting the articulating curette 10 into the cannula 50; manipulating the controller 13 to longitudinally axially move the decorticating head 18 into position as depicted in FIGS. 11-14; removing vertebral endplate material or decorticating a vertebral endplate from the vertebral endplate (not shown) of the vertebra (not shown) of the spine (not shown); retracting the decorticating head 18 into the cannula; and removing the articulating curette 10 from the cannula 50.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention.

What is claimed is:

1. A medical instrument for decorticating a vertebral endplate of a vertebra of a spine via a cannula during a surgical spine procedure comprising:
   a handle;
   a controller connected to the handle;
   a first arm extending from the controller and defining a first arm distal end;
   a second arm extending from the controller opposite to the first arm and defining a second arm distal end;
   a control shaft defining a control shaft distal end, a control shaft proximal end, and a longitudinal axis, the control shaft disposed between the first and second opposing arms, the control shaft proximal end operably coupled to the controller for longitudinally axial movement of the control shaft by the controller relative to the first and second opposing arms;

a decorticating head for decorticating a vertebral endplate of a vertebra, the decorticating head having an end surface, an upper surface, a lower surface opposite the upper surface, a first lateral side surface between the upper surface and the lower surface, and a second lateral side surface between the upper surface and the lower surface and opposite to the first lateral side surface, a first single blade extending along a first side length of the upper surface and projecting laterally outward from the first lateral side surface, and a second single blade extending along a second side length of the upper surface opposite the first single blade and projecting laterally outward from the second lateral side surface, the decorticating head and pivotally connected to the first arm distal end and the second arm distal end via a single pivot for 90° articulation about the first arm and the second arm; and a pivot mechanism situated on and between the decorticating head and the control shaft distal end and configured to provide controlled articulation of the decorticating head through longitudinally axial movement of the control shaft.

2. The medical instrument of claim 1, wherein the first single blade and the second single blade are each configured to decorticate a vertebral endplate when the decorticating head is pivoted from 0° to 90°, relative to the longitudinal axis of the control shaft.

3. The medical instrument of claim 2, wherein the decorticating head defines a decorticating head proximal end and a decorticating head distal end, and includes a hole at the decorticating head proximal end adjacent the first and second blades.

4. The medical instrument of claim 3, wherein the pivot mechanism includes a slot situated in the decorticating head distal end, and a post situated in the control shaft distal end and extending into the slot.

5. The medical instrument of claim 4, wherein the slot is angled relative to the longitudinal axis of the control shaft.

6. An articulating curette for decorticating a vertebral endplate of a vertebra of a spine during a surgical spine procedure comprising:

a handle;
a controller connected to the handle;
a shaft assembly including:
   two opposing arms extending from the controller and defining two arm ends distal to the controller; and
   a control shaft defining a distal control shaft end and a proximal control shaft end and disposed between the two opposing arms, the control shaft proximal end operably coupled to the controller for longitudinally axial movement of the control shaft by the controller relative to the two opposing arms;

a decorticating head for decorticating a vertebral endplate of a vertebra, the decorticating head having an end surface, an upper surface, a lower surface opposite the upper surface, a first lateral side surface between the upper surface and the lower surface, and a second lateral side surface between the upper surface and the lower surface and opposite to the first lateral side surface, a first single blade extending along a first side length of the upper surface and projecting laterally outward from the first lateral side surface, and a second single blade extending along a second side length of the upper surface opposite the first single blade and projecting laterally outward from the second lateral side surface, the decorticating head pivotally connected to the two arm ends of the two opposing arms via a single pivot for 90° articulation about the two opposing arms; and a pivot mechanism situated on and between the decorticating head and the control shaft distal end for providing controlled articulation of the decorticating head through longitudinally axial movement of the control shaft.

7. The articulating curette of claim 6, wherein the first single blade and the second single blade are each configured to decorticate a vertebral endplate when the decorticating head is pivoted from 0° to 90°, relative to the longitudinal axis of the control shaft.

8. The articulating curette of claim 7, wherein the decorticating head defines a decorticating head proximal end and a decorticating head distal end, and includes a hole at the decorticating head proximal end adjacent the first single blade and the second single blade.

9. The articulating curette of claim 8, wherein the pivot mechanism includes a slot situated in the decorticating head distal end, and a post situated in the control shaft distal end and extending into the slot.

10. The articulating curette of claim 9, wherein the slot is angled relative to the longitudinal axis of the control shaft.

11. A method of decorticating a vertebral endplate of a vertebra of a spine comprising:

making an incision in a body of a patient adjacent desired vertebrae;
inserting a cannula in the incision;
inserting an articulating curette in the cannula, the articulating curette having:
   a handle;
   a controller connected to the handle;
   a shaft assembly including:
      two opposing arms extending from the controller and defining two arm ends distal to the controller; and
      a control shaft defining a distal control shaft end and a proximal control shaft end and disposed between the two opposing arms, the control shaft proximal end operably coupled to the controller for longitudinally axial movement of the control shaft by the controller relative to the two opposing arms;
   a decorticating head for decorticating a vertebral endplate of a vertebra, the decorticating head having an end surface, an upper surface, a lower surface opposite the upper surface, a first lateral side surface between the upper surface and the lower surface, and a second lateral side surface between the upper surface and the lower surface and opposite to the first lateral side surface, a first single blade extending along a first side length of the upper surface and projecting laterally outward from the first lateral side surface, and a second single blade extending along a second side length of the upper surface opposite the first single blade and projecting laterally outward from the second lateral side surface, the decorticating head pivotally connected to the two arm ends of the two opposing arms via a single for 90° articulation about the two opposing arms; and
   a pivot mechanism situated on and between the decorticating head and the control shaft distal end for providing controlled articulation of the decorticating head through longitudinally axial movement of the control shaft;

operating the articulating curette to decorticate the vertebral endplate by the decorticating head when the decorticating head is pivoted from 0° to 90°, relative to the longitudinal axis of the control shaft; and removing the articulating curette from the cannula.

12. The method of claim 11, wherein the decorticating head of the articulating head defines a decorticating head proximal end and a decorticating head distal end, and includes a hole at the decorticating head proximal end adjacent the first single blade and the second single blade.

13. The method of claim 12, wherein the pivot mechanism of the articulating curette includes a slot situated in the decorticating head distal end, and a post situated in the control shaft distal end and extending into the slot.

14. The method of claim 12, wherein the slot of the pivot mechanism of the articulating curette is angled relative to the longitudinal axis of the control shaft.

\* \* \* \* \*